United States Patent [19]

Braun et al.

[11] 4,074,971

[45] Feb. 21, 1978

[54] APPARATUS AND METHOD FOR THE PHARMACOLOGICAL MANIPULATION OF THE COAGULATION MECHANISM IN BLOOD AND FOR SIGNALLING THE EVENT OF BLOOD COAGULATION

[75] Inventors: Walter Jacob Braun; John Henry Altshuler, both of Englewood; Peter Whitfield Cherry, Boulder, all of Colo.

[73] Assignee: HemoTec, Inc., Englewood, Colo.

[21] Appl. No.: 649,649

[22] Filed: Jan. 16, 1976

[51] Int. Cl.$^2$ ............................................. G01N 33/16
[52] U.S. Cl. ................................... 23/230 B; 73/64.1; 356/39
[58] Field of Search ........................ 23/230 B; 73/64.1; 356/39, 246

[56] References Cited

U.S. PATENT DOCUMENTS

| | | | |
|---|---|---|---|
| 3,307,392 | 3/1967 | Owen et al. | 23/230 B X |
| 3,450,501 | 6/1969 | Oberhardt | 23/230 B X |
| 3,713,780 | 1/1973 | Shapiro | 23/259 |
| 3,854,324 | 12/1974 | Altshuler et al. | 23/230 B X |

*Primary Examiner*—Robert M. Reese
*Attorney, Agent, or Firm*—Gary M. Polumbus

[57] ABSTRACT

An apparatus and method for accelerating the coagulation of blood and the components thereof uses the injection of an additive and gas to trigger coagulation. The appartus is designed to include a disposable multi-cell pack for minimizing manual handling of the blood and for minimizing exposure thereof to foreign surfaces with each cell containing a specimen of blood disposed above, but separated from, a predetermined amount of additive by means of a releasable cap. The cell pack containing the multiplicity of cells is inserted over a corresponding multiplicity of gas injection nozzles which effect the release of the caps in each cell for injecting the additive and the gas into the blood. As the gas passes through the blood, bubbles that are continually formed in the space above the blood burst and blood transported therein refluxes back into the blood below until coagulation occurs. A first photocell detector determines whether bubbles are formed above the surface of the blood and generates a signal if no bubbles exist due to a gas flow failure. When the blood commences to coagulate, the blood transported in the bubbles becomes gel-like and the transported blood rather than refluxing downwardly becomes trapped in a gauze disposed in the space above the main body of blood. In response to the collection, the level of the main body of blood drops which is detected by a second photocell detector thereby signalling the event of coagulation.

51 Claims, 15 Drawing Figures

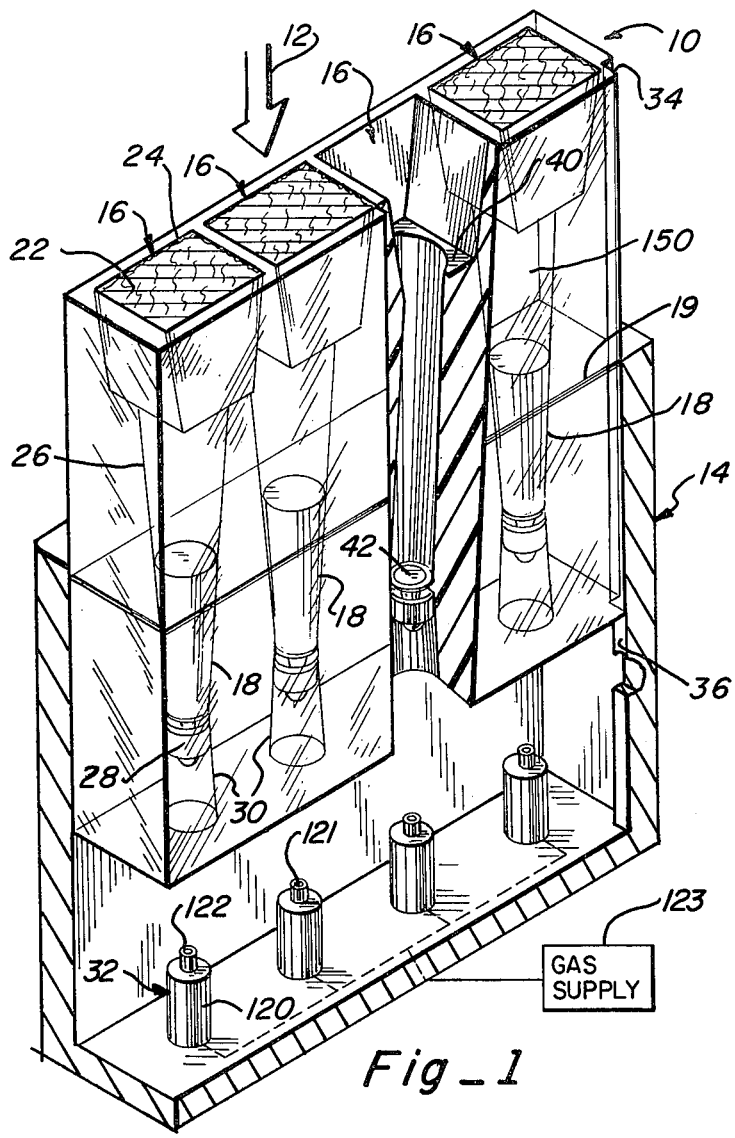
Fig_1
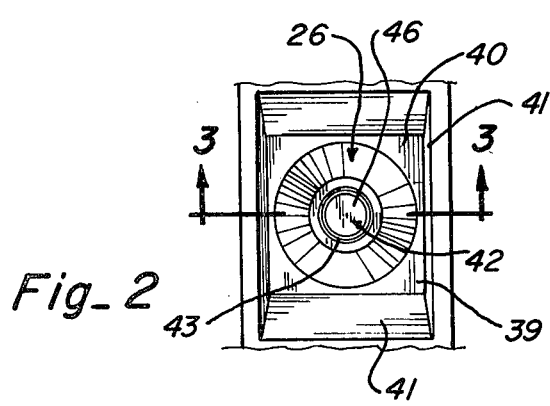
Fig_2
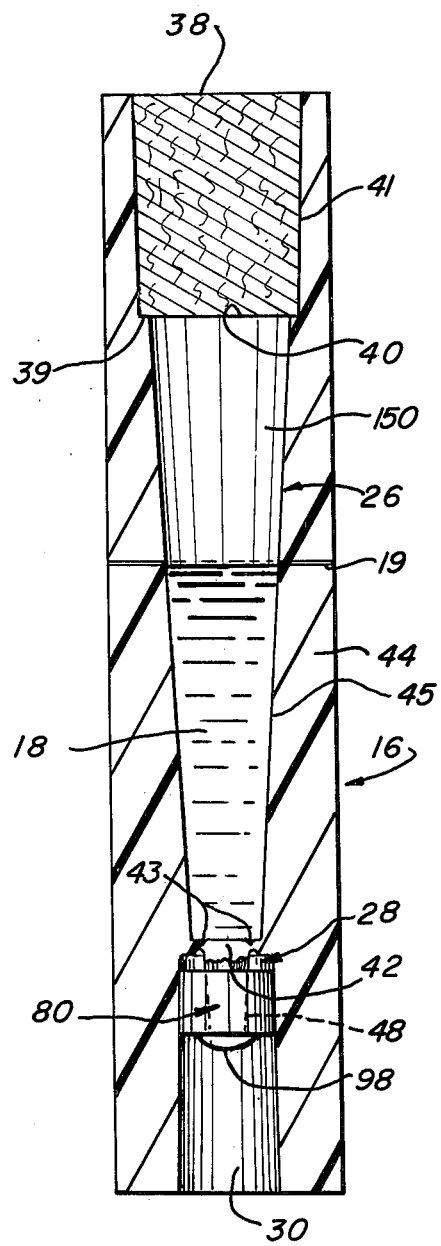
Fig_3

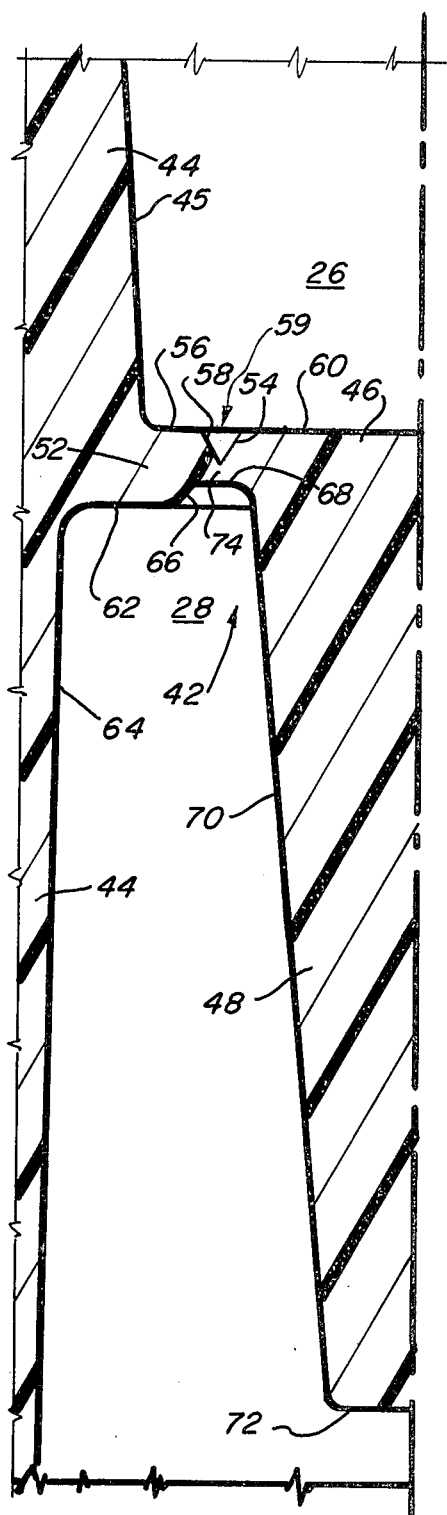
Fig_4
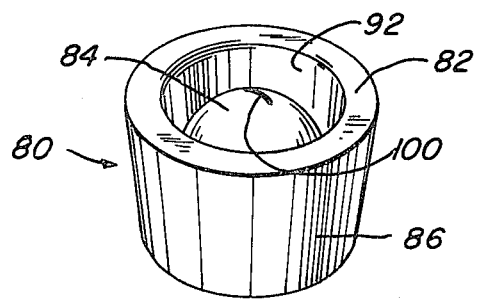
Fig_5
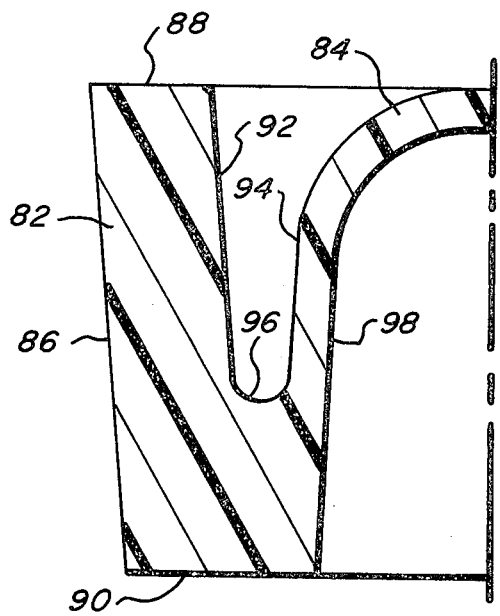
Fig_6
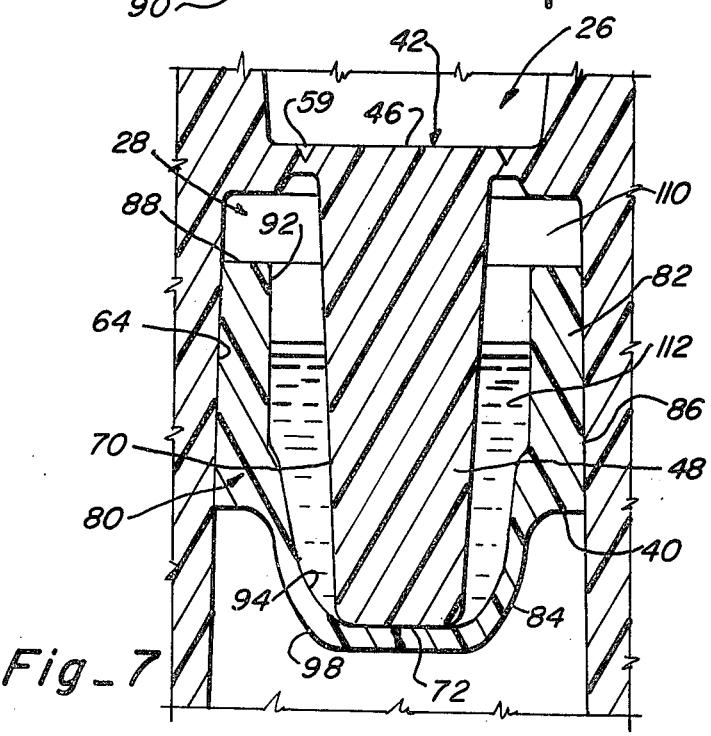
Fig_7

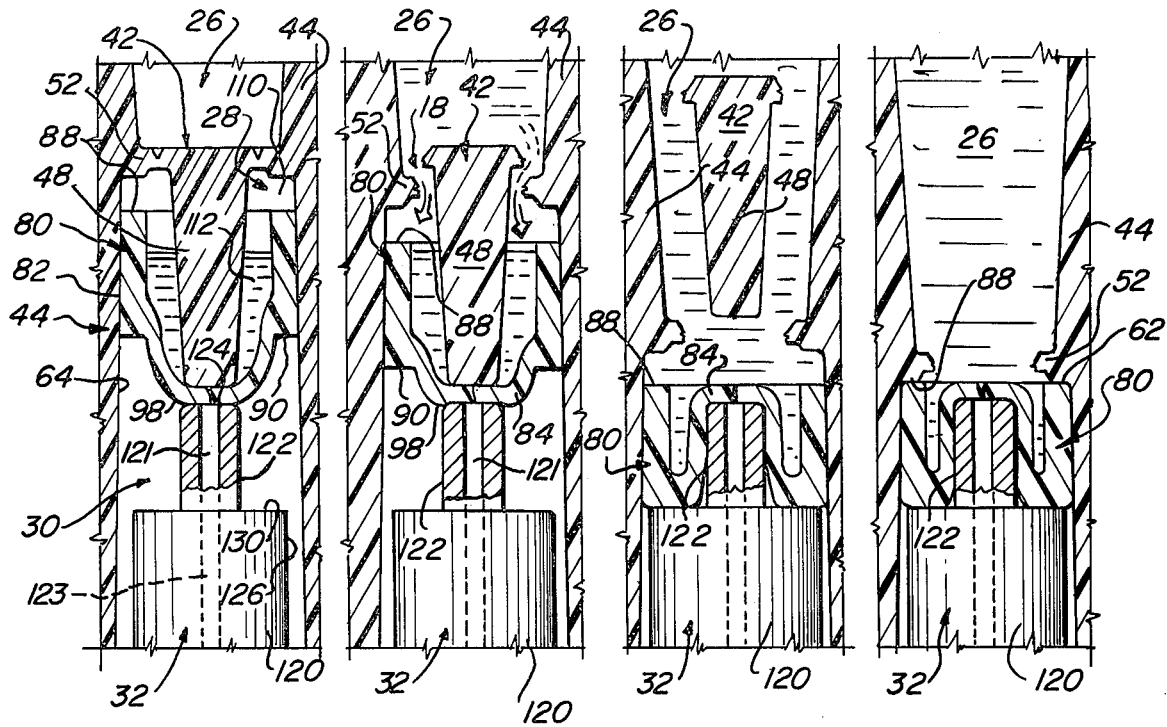
Fig_8  Fig_9  Fig_10  Fig_11
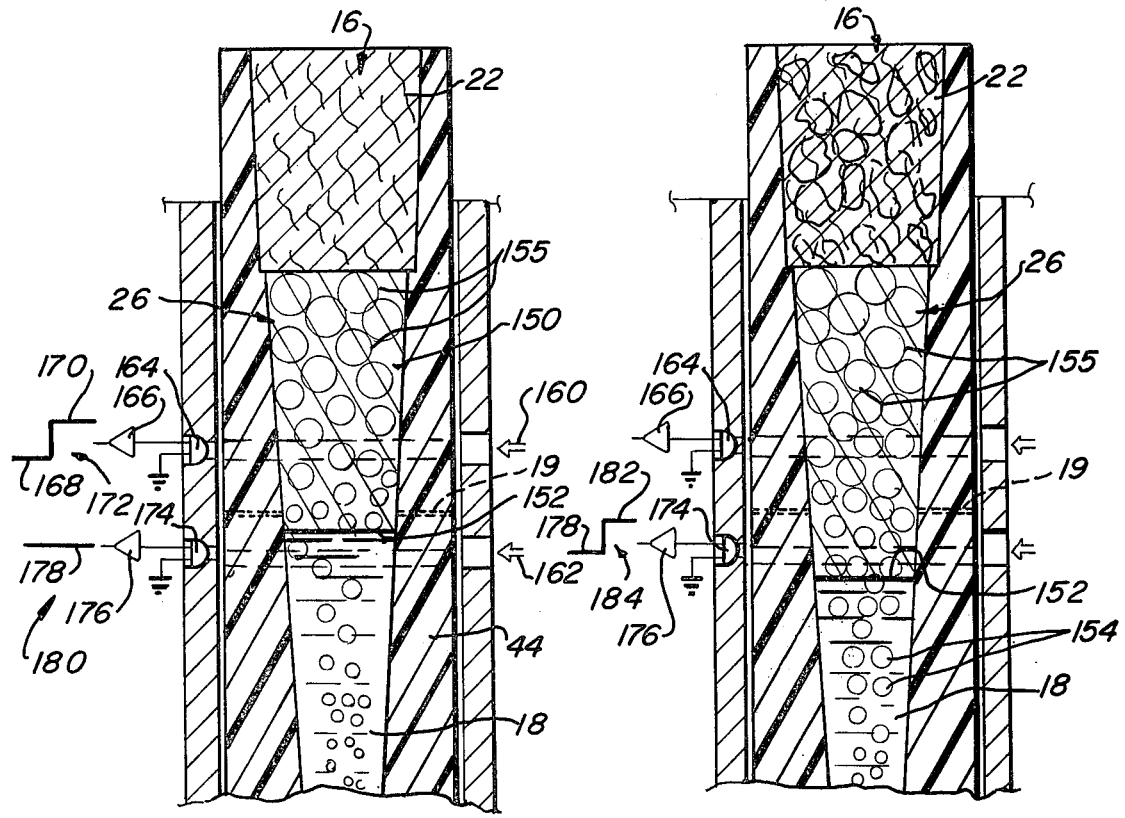
Fig_14  Fig_15

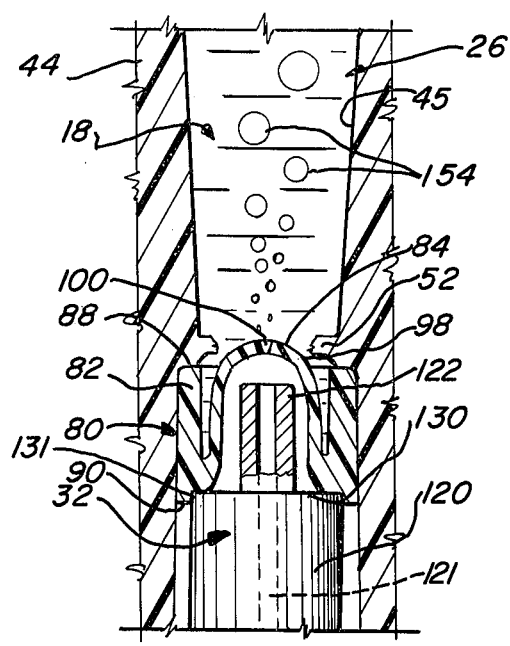
Fig_12
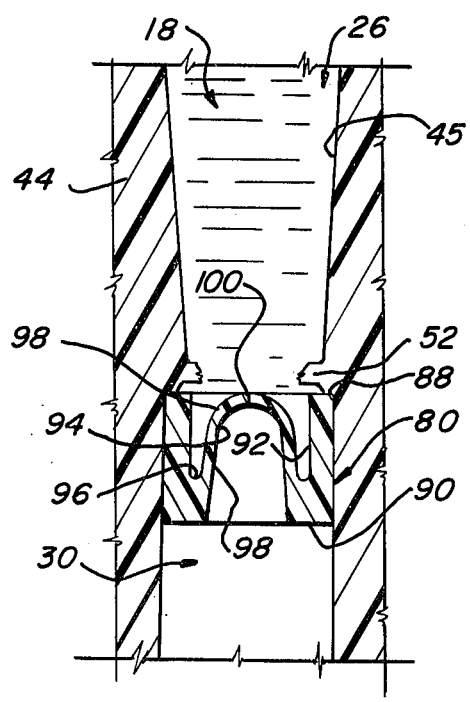
Fig_13

APPARATUS AND METHOD FOR THE PHARMACOLOGICAL MANIPULATION OF THE COAGULATION MECHANISM IN BLOOD AND FOR SIGNALLING THE EVENT OF BLOOD COAGULATION

BACKGROUND OF THE INVENTION

1. Field of the Invention

The present invention relates generally to an apparatus and method for accelerating and signalling the event of coagulation of blood and components thereof.

This invention relates more particularly to an apparatus and method for injecting a neutralizing additive into a sample of anticoagulated blood and components thereof and, after neutralization, for accelerating and signalling the event of coagulation.

2. Description of the Prior Art

Lengthy surgical procedures, especially those requiring temporary cardiopulmonary bypasses and total body perfusion, involve blood coming into contact with many foreign surfaces, thereby necessitating pharmacological manipulation of the coagulation mechanism to prevent coagulation of the blood and its resultant catastrophic effects. It is known in the art of perfusion, that blood coagulation is a hemostatic process wherein certain factors normally passive in the bloodstream are stimulated into an active form which trigger a chemical chain of events resulting in a blood clot. A blood clot comprises a mass of fibrin threads surrounding entrapped cells. The process of coagulation is not completely understood, but it is well known in the art that coagulation occurs when blood is removed from the body and passed for example, through an extracorporal circuit.

In order to prevent coagulation during an extracorporeal bypass, various drugs may be injected into the blood. For example, sodium heparin is usually injected into patients requiring open heart surgery in order to neutralize the clotting factors. Open-heart surgery exposes blood to numerous procoagulant stimuli and requires significantly more heparin than other surgical procedures to achieve anticoagulation. Since, heparin is metabolized rapidly it has a half-life of one to two hours, and injections of heparin must be continuously made during surgery. Too little heparin will cause the diastrous effect of coagulation while too much heparin will cause an equally diastrous effect of postoperative internal bleeding or hemorrhaging.

The use of heparin and its half-life characteristics are well known in the art as found, for example, in Wright, et al, "Heparin Levels During and After Hypothermic Perfusion", 5 T. Card. Surg. 244–250 (1964).

A properly heparinized patient, therefore, has a concentration of heparin in his blood that is sufficient to prevent coagulation of blood but not great enough to cause internal bleeding. A surgeon, after acquiring experience, develops an insight for the amounts of heparin to use and when to inject additional heparin based on such parameters as height, weight, sex and blood volume of the patient. Obviously, such an approach involves a high degree of risk-taking by the patient.

After surgery is completed it becomes necessary to neutralize the heparin to prevent postoperative internal bleeding by the injection of an appropriate additive such as protamine sulfate. If administered alone, protamine is an anticoagulant. However, when given in the presence of heparin, a stable and physiologically inert salt is formed, thus neutralizing the anticoagulant activity of both drugs. Accurate determination of the amount of protamine for neutralization is required since too little or too much protamine results in anticoagulated blood and possible postoperative bleeding. The use of protamine as a postoperative neutalizer is well known in the art; see, for example, Reed & Clark, Cardiopulmonary Perfusion (1975), Library of Congress Catalog Card Number 75-7168.

After the patient is neutralized a "heparin rebound" condition may arise in which the patient's blood becomes heparinized due to a reappearance of heparin. Although heparin rebound is not fully understood, it is well known in the art, see Ellison, et al, "Heparin Rebound", 67 J. Thoracic Card. Surg. 723–729 (1974).

Heparin is commercially provided in varying concentrations depending on its potency from a variety of sources such as beef lung, beef liver, beef mucosa, and pork mucosa. Protamine is also commercially available in a variety of concentrations also emanating from a variety of sources such as the sperm of salmon and certain other fish.

The classical method of determining blood coagulation time is to determine the Lee-White clotting time. A sample of blood is inserted into a centrifuge in order to separate the serum from the blood. The serum is then inserted into a testing machine which determines the coagulation time by detecting a change in the opaqueness of the serum. The Lee-White process is a long process generally taking thirty minutes or longer and which involves excessive manual handling on foreign surfaces of the blood and the use of a centrifuge and a separate testing machine. The Lee-White method is not practical for determining clotting time parameters of anticoagulated blood.

A conventional approach for determining the amount of protamine at the conclusion of a heart-lung extracorporeal bypass is the protamine titration method as disclosed, for example, in Hurt, et al, "The Neutralization of Heparin by Protamine in Extracorporeal Circulation", 32 J. Thoracic Card. Surg. 612–619 (1956). The protamine titration method is a developed laboratory skill and involves using test tubes, known titration techniques, and visually determining the event of coagulation. The titration normally takes 15–20 minutes and is a function of the lab technician's skill.

Another conventional prior art approach uses a test tube sample of the heparinized blood in which is manually injected via a hypodermic needle a known amount of protamine. A gas is injected into the test tube mixture to accelerate coagulation, the gas acts as a foreign body which stimulates the clotting factors. When the blood coagulates a back pressure is delivered into the gas delivery system which is sensed by a pressure detector. The above approach is disclosed in Altshuler, et al, "Hemotensiometry", 18 Annals of Thoracic Surg. 516–530 (1974).

The above prior art approaches are generally primarily dependent on operator skill, and are, therefore, highly nonreproducible. In addition, the prior art approaches are slow in measuring the event of coagulation. At the conclusion of surgery involving an extracorporeal bypass, hemorrhage-related morbidity and mortality poses a constant threat to the heparinized patient. Although protamine and other additives effectively neutralize heparin, an overdose of protamine may cause internal bleeding, shock or thrombocytopenia. A patient who is rapidly neutralized after disconnecting the bypass and during the rebound stage will be in a minimum risk condition. If post operative hemmorrhaging then occurs, the cause is abnormal and generally mechanical thereby requiring further re-exploration.

OBJECTS OF THE INVENTION

The present invention has for its primary object provision of a novel apparatus and method for signalling the event of coagulation of blood and components thereof.

It is another object of the present invention to provide a novel apparatus and method for injecting a predetermined amount of neutralizing additive into a sample of anticoagulated blood and components thereof and for signalling the event of coagulation.

It is a further object of the present invention to provide a novel apparatus and method which minimizes manual handling of a blood specimen during coagulation measurement thereof.

It is a further object of the present invention to provide a novel disposable apparatus containing a plurality of cells each of which contains an identical amount of the same blood specimen.

It is still a further object of the present invention to provide a novel apparatus wherein predetermined amounts of a neutralizing additive are injected into an anticoagulated blood sample thereby minimizing possible human error.

It is still a further object of the present invention to provide a novel apparatus and method for detecting the event of coagulation through injection of gas into the blood specimen.

It is still a further object of the present invention to provide a novel apparatus for the introduction of a neutralizing additive into anticoagulated blood through use of injected gas.

It is still a further object of the present invention to provide a novel apparatus comprising the storage of a specimen of anticoagulated blood positioned above, but releasably separate from, a predetermined amount of neutralizing additive.

It is still a further object of the present invention to provide a novel apparatus for signalling the event of coagulation comprising the positioning of the specimen anticoagulated blood above, but separate from, a predetermined amount of neutralizing additive; and further comprising apparatus for releasing a diaphragm separating the blood from the additive and for injecting gas at a predetermined rate into the additive and blood mixture.

It is still a further object of the present invention to provide a novel apparatus for signalling the event of coagulation of anticoagulated blood by providing means for the storage of the specimen blood separate and apart from a predetermined amount of neutralizing additive until the injection of a gas into the blood in order to mix the additive with the blood to neutralize the effect of the anticoagulant and to introduce gas as a foreign object in order to accelerate the event of coagulation and to form bubbles on the surface of the blood, said apparatus further having gas fail-safe means for determining the presence of the bubbles, means for collecting the coagulated blood above the surface of the blood when the liquid blood in the bubbles becomes gel-like at the point of coagulation, and means for detecting the level of the blood at the point of coagulation.

THE DRAWING

The invention possesses other advantageous features, some of which, with the foregoing, will be set forth at length in the following description where those forms of the invention which have been selected for illustration in the drawing accompanying and forming a part of the present specification, are outlined in full. In said drawing, one form of the invention is shown, but it is to be understood that it is not limited to such form, since the invention as set forth in the claims may be embodied in other forms.

Referring to the drawings:

FIG. 1 is a partial perspective view of the four-cell cell pack of the present invention being inserted into the channel analyzer of the present invention.

FIG. 2 is a top planar view of one cell of the cell pack of FIG. 1.

FIG. 3 is a sectional view of FIG. 2 illustrating the components of one cell.

FIG. 4 is a partial sectional view of the releasable cap of the present invention.

FIG. 5 is a perspective view of the plug of the present invention in a normal unstressed configuration.

FIG. 6 is a partial center-line sectional view of the plug of FIG. 5.

FIG. 7 is a sectional view of the releasable cap and plug forming a chamber of the present invention.

FIG. 8 is a sectional view of the nozzle of the present invention abutting the plug in the position shown in FIG. 7.

FIG. 9 is a sectional illustration of the releasable cap breaking away due to an upward force by the nozzle of the present invention.

FIG. 10 is a sectional illustration showing the nozzle in abutting communication with the plug of the present invention.

FIG. 11 is a sectional illustration showing the plug abutting the bottom of the vial of the present invention.

FIG. 12 is a sectional illustration showing the thin hemispherical portion of the plug ballooning upwardly and opening a slit defined therein to permit passage of gas.

FIG. 13 is a sectional illustration showing the plug in a stressed position with the slit defined therein held closed.

FIG. 14 is a sectional illustration showing the transportation of liquid blood in bubbles formed above the surface of the blood.

FIG. 15 is a sectional illustration showing the transportation of gel blood in bubbles into the gauze of the present invention for entrapment thereof.

SUMMARY OF THE INVENTION

The foregoing and other objects are obtained in accordance with the apparatus and method of the present invention whereby specimens of blood and components thereof are collected and stored in a disposable compact cell pack having a plurality of cells each of which contains the same amount of blood. The cell pack containing the blood specimen cooperates with a channel analyzer of the present invention to automatically inject an additive into the blood in each cell and further to inject gas as a foreign object into the blood and additive mixture in order to trigger coagulation. The injected gas further creates bubbles of liquid blood above the surface of the blood. At the point of coagulation, the blood becomes gel-like and the blood transported by the bubbles is trapped above the surface of the remaining blood causing the level of the remaining blood to drop. A detection apparatus senses the level change and generates an electrical signal indicative of coagulation.

The cell pack contains a plurality of individual cells in a compact relationship and is designed to be disposable after use. Each cell comprises an upper hopper containing a gauze-like material, a vial disposed below but in fluid communication with the hopper for containing the blood sample, a downwardly protruding passageway separated from the vial by a releasable cap, a plug disposed in the passageway for defining a collapsible chamber between the cap and the plug, said chamber containing a predetermined amount of the additive.

The channel analyzer is uniquely designed to encourage the coagulation of blood in each of the separate cells. A plurality of upstanding injection nozzles are provided to mate with the downwardly protruding passageways of the cell pack to release the cap and to collapse the chamber thereby injecting the additive into the blood. Gas, from a constant supply, is delivered via the separate injection nozzles, into the blood of each cell in order to accelerate coagulation. The channel analyzer includes two light sensitive detectors for each cell, the first detector determines whether or not gas is being injected into the cell by detecting the presence of bubbles above the surface of the blood and the second detector determines whether or not the level of the blood has dropped due to coagulation. The first light sensitive detector generates a signal for activation of a fail-safe warning system in the event that no bubbles are detected in any one cell. The second light sensitive detector generates a signal at the event of blood coagulation.

In operation, blood is injected into the cells of the disposable cell pack of the present invention to a predetermined level. The passageway of each cell is then inserted into the channel analyzer over the corresponding injection nozzle. The injection nozzle abuts the chamber containing the additive and effectuates the release of a cap separating the blood from the additive. The injection nozzle further collapses the chamber thereby injecting the additive into the blood. The chamber forms a gas-tight seal with the nozzle and the gas is injected into the blood and additive mixture through a pressure expanded slit in the bottom of the chamber. A buildup of bubbles occurs in the space above the level of the blood, the bubbles rupture and release liquid blood which refluxes downwardly back into the blood. The first detector responds to a lack of bubbles above the blood to effect a warning signal indicative of a failure in gas flow for the cell. After a time interval, the blood in the bubbles, due to the presence of the gas, commences to coagulate and becomes gel-like in composition. At the point of coagulation, the gel-like blood in the bubbles accumulates in the gauze. No downward refluxing of the gel-like blood occurs. The bubbles, therefore, act as a transport mechanism in transporting liquid blood downwardly into the sample before coagulation and for transporting gel-like blood upwardly into the gauze after coagulation. The collection of gel-like blood by the gauze reduces the level of the liquid blood in the bottom of the cell to a level at which light transmits into the second detector with greatly increased intensity. The signal at the output of the second detector is indicative of the event of coagulation.

DESCRIPTION OF THE PREFERRED EMBODIMENT

The cell pack 10 of the present invention, shown in FIG. 1, is inserted downwardly in the direction of the arrow 12 into a channel analyzer 14 of the present invention. The cell pack 10 includes a plurality of individual cells 16 each of which contains an identical amount of body fluid 18, such as blood and components thereof, filled to a predetermined level 19. Each cell 16 comprises a cavity 24 for holding a gauze-like material 22, a vial 26 for holding the body fluid specimen 18, a chamber 28 for containing an additive to be injected into the fluid 18 and a formed passageway 30 through which a nozzle 32 positioned in the bottom of the cell analyzer 14 may be inserted for injecting gas into the fluid 18.

The cell pack 10 is of integral molded construction and includes provisions for a plurality of identical cells 16 molded therein. The cell pack 10 may be manufactured from general purpose clear styrene material and may include either the solid configuration as shown in FIG. 1 or a thin walled-construction thereby eliminating all excess styrene material in order to reduce manufacturing costs.

The cell pack 10 of the present invention is of rectangular design with a plurality of cells 16 disposed along its longitudinal axis. One edge 34 of the cell pack 10 contains a guide notch mating with an outwardly protruding guide notch 36 formed in the cell analyzer 14. In this manner, the cell pack 10 can be inserted into the cell analyzer 14 in only one orientation. Any suitable guiding means can be utilized in the present invention.

An upper cavity area 24 is designed as a hopper, as shown in FIGS. 1, 2 and 3, to include an upper rectangular surface 38 which is open to the atmosphere and a lower opposing surface 39 having a circular hole formed therein defining the upper opening 40 of the vial 26. The sides 41 of the cavity 24 taper downwardly from the upper surface 38 to a shoulder 39 surrounding the circular opening 40 of the vial 26.

As will be more fully explained in the ensuing discussion, a gauze-like material 22 is inserted into the cavity 24 to partially or completely fill the cavity 24. The gauze 22 is arranged so that it does not substantially extend downwardly or into the vial 26, as shown in FIG. 3. The present invention preferably utilizes conventional polymeric gauze. The gauze may be wetted with an appropriate wetting agent, as for example, that manufactured by the Dow-Corning Corp. as ANTI-FOAM A. The use of Dow-Corning Anti-Foam A as a wetting agent is commonly recognized in the art as discussed in Reed & Clark, Cardiopulmonary Perfusion 236 (1975), Library of Congress No. 75-7168.

Protruding downwardly from the cavity 24 is a vial 26 having an upper enlarged circular opening 40 centered in the bottom surface of the cavity 24 and having a lower narrow circular formed cap 42. The sides 45 of the vial 26 may taper at an angle with respect to vertical to form a downwardly pointing truncated cone. The preferred embodiment utilizes taper angles preferably between 0.5° to 10° from vertical and the sides 44 are preferably linear from the upper circular opening 40 to the lower circular cap 42. The cap 42, integral with the wall 44 of the vial 26 and, as shown in FIGS. 3, 4 and 7, includes an upper circular diaphragm 46 and a lower protruding stem 48 centrally disposed on the under surface 68 of the diaphragm 46.

As shown in FIG. 4, the wall 44 has an inwardly protruding circular flange member 52 integral with the outer circular edge 54 of diaphragm 46. The downwardly tapering circular sides 45 of the vial 26 terminate into a substantially horizontal shoulder 56 of the circular flange 52. The shoulder 56 terminates in a downwardly extending tapered edge 58. The downwardly tapered circular edge 58 of the flange 52 terminates in the upwardly directed tapered edge 54 of the diaphragm 46. The upper surface 60 of the diaphragm 46 lies in substantially the same horizontal plane as the shoulder 56. The two edges 58 and 54 form a V-shaped circular channel 59 encircling the diaphragm 46.

Opposing shoulder 56 on flange 52 is a bottom shoulder 62 which outwardly extends to and is integral with wall 44 on surface 64 of chamber 28. As will be more fully discussed in the ensuing, surface 64 of chamber 28 upwardly tapers at preferably 0.5° towards cap 42. Shoulder 62 is substantially horizontal and joins the slightly tapering surface 64 at a point outward from the juncture of shoulder 56 with surface 45. The inward wall 66 of shoulder 62 upwardly tapers at preferably 30° towards the diaphragm 46 into a substantially horizontal bottom surface 68. Inwardly tapering wall 66 is disposed slightly outward from the V-shaped circular channel 59 and the surface 68 is disposed slightly below the V-shaped channel 59. Surface 68 inwardly continues to a point just past the V-shaped channel 59 whereupon it joins a downwardly extending surface 70 which forms the side walls of the stem 48. The stem 48 terminates in a horizontal surface 72. The above-described cap 42 and flange 52 is designed to releasably seal chamber 28 from vial 26. As will be more fully discussed, the cap 42 under an upwardly directed pressure on surface 72 of the stem 48 is designed to break away from the circular wall 44 at the circular region 74 disposed between the V-shaped channel 59 and surface 68.

Disposed just below cap 42 and contained by surfaces 64 of wall 44 is a plug 80 for defining chamber 28 in passageway 30 as shown in FIG. 3. Before discussing the use of plug 80 in the cell 16 of the present invention, it is necessary to first describe the characteristics of the plug removed from the cell 16 as it exists in its natural state as shown in FIGS. 5 and 6. The plug 80 is preferably molded from soft plastic material, such as shell Krayton, to include a thick circular side wall 82 and a relatively thin hemispheric portion 84. The thick outer wall portion 82 has upwardly and outwardly extending, at preferably 0°- 5°, side surfaces 86 terminating in substantially horizontal top and bottom surfaces 88 and 90. The upper surface 88 connects to a downwardly extending inner surface 92 substantially in parallel with the outer surface 86 and joins an inwardly and upwardly directed surface 94 of the hemispherical portion 84 after undergoing a substantially 180° bend at point 96. The bottom horizontal surface 90 of wall 82 inwardly extends beyond the reverse bend 96 and connects to the upwardly directed inner surface 98 of the hemispherical portion 84. Surface 98 is substantially in parallel with the upper surface 94 at preferably 6° from vertical. A slit 100 is centrally disposed at the apex of the hemispherical portion 84.

The use of the plug 80 in the present invention is as follows. In the manufacture of the cell pack 10, the cell pack 10 is positioned so that passageways 30 are pointed upwardly. A predetermined amount of desired additive, preferably 0.1 to 0.5 cc is deposited into each passageway 30. In this orientation the additive rests against surface 68 of cap 42 and the surface 62 of flange 52. Plug 80 is inserted into passageway 30 with surface 88 directed towards the surface 62. The plug 80 as it traverses the length of passageway 30 wipes surfaces 64 clean of the additive and seals the additive into a now-defined chamber 28. The chamber 28, as shown in FIG. 7, contains a gas space 110 and the additive 112. The diameter of the plug 80 is slightly greater than the diameter of the passageway 30 in order to form an effective seal to prevent leakage of the additive 112 therefrom. As mentioned, the surfaces 64 of passageway 30 are inwardly tapered and the surfaces 86 of the plug 80 are outwardly tapered, therefore, the further the plug 80 traverses in the passageway 30 the greater the compressive forces become to form an effective seal. The plug 80 is positioned in passageway 30 so that surface 72 of stem 48 abuts the surface 94 of hemispherical portion 94 and causes it to invert in the manner as shown in FIG. 7. In this arrangement, the hemispherical portion 84 is under considerable stress from action from stem 48 and the slit 100 is held firmly in a closed position by the elastic stresses found within the plug 80. The hemispherical portion 84 is forced into the inverted state as shown in FIG. 3, the hemispherical portion 84 extends preferably slightly below surface 90 of the side walls 82. For purposes of clarity in illustration, however, FIGS. 7 and 8 illustrate the hemispherical portion exhibiting greater inversion. Surface 90, in this configuration, inwardly connects with the now downwardly protruding surface 98 of the hemispherical portion 84 while surface 92 connects with a now downwardly extending surface 94. In this configuration, the reverse bend 96 as shown in FIG. 6 has been elastically transformed into a flattened downwardly extending surface. The plug 80 defines a sealed chamber 28 containing gas 110 and additive 112. It is to be noted, that the cell pack 10 of the present invention is manufactured to include plug 80 in the configuration as shown in FIG. 7 containing the predetermined amount of additive 112. Such an arrangement can be conveniently transported over long distances and conveniently stored for periods of time with no loss or leakage of the additive 112 from the chamber 28.

When the cell pack 10 is desired to be utilized, specimens of blood 18 are injected into each cell 16 by means of a hypodermic needle, not shown, inserted through the gauze 22 as shown in FIG. 1. After injection of the blood 18 into the cell 16, cell pack 10 is inserted into the channel analyzer 14 of the present invention wherein each cell 16 engages an upstanding cylindrically shaped nozzle 32. The cylindrical portion 120 of each nozzle 32 is designed to be substantially the same length as passageway 30 in a manner more fully discussed later. Disposed on the upper surface 130 of cylinder 20 is an upstanding injection needle 122. The injection needle 122 is cylindrically shaped and centrally located on the upper surface of the cylindrical portion 120. A passageway 121 is centrally located and extends through both the cylinder 120 and the needle 122 for access to a supply of gas from a conventional gas source 123, shown schematically. One type of a conventional gas supply may be a motor driving a plurality of pumps. The diameter of the cylindrical portion 120 is preferably somewhat less than the diameter of the passageway 30 as shown in FIG. 8. The height of the needle portion 122 is preferably approximately equal to the height of the hemispherical portion 84 in relation to the bottom surface 90 of plug 80 as the plug 80 exists naturally as presented in FIGS. 5 and 6.

Reference will now be made to FIGS. 8 through 12 for a discussion of the interaction of nozzle 32 with plug 82 and cap 42 of the present invention. FIGS. 8 through 12 illustrate the successive stages during the insertion of cell pack 10 into the channel analyzer 14 in the direction of arrow 12. In FIG. 8, the nozzle 32 is shown in which the upper surface 124 of the needle 122 slightly abuts surface 98 of the hemispherical portion 84 of the plug 80. It is to be noted that the diameter of needle 122 is preferably equal to the diameter of the hemispherical portion 84 at its mid-region. The sides 126 of the cylindrical portion 120 of the nozzle 32 are in close relation to surface 64 of passageway 30. In FIG. 9, additional downward travel of the cell pack 10 over the nozzle 32 causes the cap 42 to break away from shoulders 52 thereby effectuating downward flow of the blood 18 to the additive 112. At this point, the hemispherical portion 84 is substantially deformed. In FIG. 10, continued downward travel by the cell pack 10 over the nozzle 32 causes the stem 42 to be ejected upwardly so that the blood 18 fully contacts the additive 112 and slight mixing thereof occurs. The hemispherical portion 84 is now in its natural position, as shown in FIGS. 5 and 6, and the upper surface 130 of the cylinder 120 slightly abuts the bottom surface 90 of the side walls 82 of the plug 90. Further downward advancement of the cell pack 10 over nozzle 32 into the passageway 30, as shown in FIG. 11, causes the upper surface 88 of plug 80 to abut the lower surface 62 of the shoulder 52. The plug 80 undergoes maximum compressive forces directed towards the center of the plug 80 at this point, due to the outwardly tapering surfaces 86 of plug 80 and the inwardly tapering surfaces 64 of wall 44 as previously mentioned. Such compressive forces cause the plug 80 to firmly seat in passageway 30 against shoulder 52. Simultaneously the upward travel of plug 80 has injected substantially all of the additive in chamber 28 into the blood 18.

Additional travel of the cell pack 10 downwardly over nozzle 32, as shown in FIG. 12, finally causes the upper surface 130 of the nozzle 32 to further deform the plug 80 by travelling upwardly into surface 90 a given distance 131. The deformed abutment of the cylinder 120 with the plug 80 on surface 90 forms a gas-tight seal between the inner surface 98 of the hemispherical portion 84 and the upper surface 130 of the cylindrical portion 120 of nozzle 32. In this manner, the hemispherical portion 84, under pressure of exiting gas 154 from passageway 121 in needle 122 balloons upwardly causing the slit 100 to open. Should the gas fail, or should the cell pack 10 be removed from the channel analyzer 14, the hemispherical portion 84 returns to its natural state shown in FIGS. 5 and 6 thereby closing slot 100. Due to the deformed shape of the plug 80 with wall 44, the slit 100 is held firmly closed so that no leakage of blood or additive will occur, as shown in FIG. 13.

The injection of gas 154 into the blood 18 thoroughly mixes the injected additive within the blood. Since in the above related application involving the cell pack 10 of the present invention, it is desired to know the strength of an anticoagulant within blood 18, therefore, each of the different cells 16 contains an appropriate neutralizing additive of varying strength. For example, the anticoagulant sodium heparin is conventionally added to blood for prolonged surgery (i.e. open heart surgery) in order to prevent coagulation of blood. Any heparin within the patient's blood must be neutralized after surgery by an appropriate additive such as conventional protamine sulfate. The protamine reacts with the heparin to provide a stable and physiologically inert salt, thereby neutralizing the anticoagulant activity of both drugs. For the above example, the heparinized blood would be injected into the vials 26 of each cell 16. In addition, cells 16 would contain protamine of varying strength in the collapsible chamber 28. Therefore, some of the cells 16 after injection of the protamine may have either a surplus of heparin due to insufficient protamine, or a surplus of protamine due to an excessive amount of protamine. Both heparin and protamine are anticoagulants and those cells containing an excess of either anticoagulant takes longer to coagulate. The cell wherein substantially the same amount of protamine has been injected into the heparinized blood will be the fastest to coagulate since the protamine has effectively neutralized the heparin. In the related application entitled "A Measuring System For The Pharmacological Manipulation Of The Coagulation Mechanism In Blood And For The Elapsed Coagulation Time", Ser. No. 649,648, now U.S. Pat. No. 4,000,972, it is desired to know which of the four cells 16 is the first to coagulate thereby indicating that that particular cell had the proper stength of protamine to most closely match the concentration of the heparin in the blood sample.

In this manner any anticoagulated blood and components thereof can be neutalized through injection of the corresponding neutralizing additive. However, the above described example is not intended to limit or delimit the utilization of the cell pack 10 of the present invention. In fact, the cell pack 10 and channel analyzer 14 may be utilized in research where it is desired to investigate coagulation properties of blood and other body fluids. A discussion of the detection of coagulation now follows.

After the cell pack 10 is fully inserted into the channel analyzer 14, as represented in FIG. 12, the space 150 is shown in FIG. 3, above the surface 152 of the blood 18 becomes crowded with bubbles of liquid blood 155 due to the injection of gas 154, as shown in FIG. 14. These blood bubbles 155 strike the surface 45 of the vial 26 and the bottom of the gauze 22 to burst and reflux downwardly into the blood 18. Preferably the tapered conical sides 45 of the vial 26 are tapered to allow a maximum of liquid blood, released upon bursting, to flow downwardly into the sample 18.

It is to be noted that if non-wetted gauze is utilized some of the liquid blood transported by the bubbles 155 may be retained near the bottom surface of the gauze whereas use of a wetted gauze minimizes such retention. Either type of gauze may be used in the present invention. Therefore, whether due to retention of blood in the gauze 22, due to refluxing of blood downwardly on surfaces 45, or due to the blood actually comprising the bubbles 154, the surface 152 of the blood drops slightly below the predetermined filling level 19 as shown in FIG. 14.

Two beams of light 160 and 162, conventionally generated, enter the vial 26 as shown in FIG. 14. The upper beam 160 is directed through the space 150 and into an opposing photodetector 164 whose resultant electronic signal is conventionally amplified by a detector 166. If, due to a failure of gas 154 being delivered upwardly through the nozzle 32, no liquid blood bubbles 155 are created, then the beam of light 160 would pass through the vial substantially unattenuated and into the photodetector 164. In that event, the detector 166 would change its output from a low state 168 to a high state of 170 in a conventional fashion and as graphically shown by wave pattern 172. If the gas 154 functions normally and is delivered upwardly through nozzle 32 then, under normal operation, the light beam 160 through space 150 would be so attentuated as to keep the output of the detector 166 in the low state 168. The second beam of light 162 enters the vial 26 and is significantly attenuated by the blood so that upon reaching an opposing photodetector 174, the output of the conventional detector 176 is sustained at the low state 178, as shown in wave pattern 180. As mentioned, due to the creation of the blood bubbles 155 the level 152 of the blood 18 drops slightly below the fill level 19. The beam of light 162 and the corresponding opposing photodetector 174 are oriented in a plane substantially below the filing level 19 so that the drop in the level 152 due to the bubble formation is still above the aforesaid plane.

After a period of time, the blood 18 commences to coagulate and the bubbles 155 enter a new phase in which the blood 18 and the surfaces of the bubbles become gel-like. Since the liquid phase has terminated, no refluxing of the blood occurs and the gel-like blood transported by the bubbles is driven upwardly into the hopper 24 containing the gauze. The gauze traps the gel-like blood from the bubbles and prevents the gel-like blood from falling downwardly into the blood in the vial. Thus, the event of coagulation prevents the bubbles 155 from refluxing down the side wall 44. In this manner, the outer surface of the bubbles 155 are gel-like and are carried upwardly into the gauze 22. In response, the surface 152 of the gel-like blood 18 rapidly drops below the plane in which the light beam 162 passes, as shown in FIG. 15, due to the lack of refluxing of blood. The light beam 162 now impinges upon the photodetector 174 with increased intensity causing the output of the detector 176 to rise to a high value of 182 as shown in wave pattern 184. It is noted that each cell 16 comprises a corresponding set of detectors 166 and 176, photodetectors 164 and 174, and light beams 160 and 162. Any conventional photodetection arrangement may be used. A preferable embodiment is disclosed in the co-pending application entitled "A Measuring System for the Pharmacological Manipulation of the Coagulation Mechanism in Blood and for the Elapsed Coagulation Time". It is obvious that in the above-described manner, the first of the four cells 16 to coagulate will have its corresponding detector 176 generating an electrical signal signifying the event of coagulation before any of the other detectors for the remaining cells 16. Such information is desirable, for example, since the first cell to coagulate containing the above-described heparin-protamine mixtures will be that cell in which the heparin was substantially neutralized by the protamine. Since each cell contains the additive protamine in varying strengths in chamber 28, the first cell to coagulate is indicative of the proper strength of protamine with which to neutralize a heparinize patient, for example, coming out of surgery.

It is to be noted that the cell pack 10 of the present invention may be used without providing an additive to the collapsible chamber 28 or without providing a plug. In either case, the cell pack 10 may find application as a device to measure coagulation time of uncoagulated blood.

While certain illustrative embodiments of the present invention have been shown in the drawings and described above in considerable detail, it should be understood that there is no intention to limit the invention to the specific form disclosed. On the contrary, the intention is to cover all modification, alternative constructions, equivalents and uses following within the spirit and scope of the invention as expressed in the appended claims.

We claim:

1. An apparatus for accelerating the coagulation of body fluid including blood, comprising:
    means for holding said body fluid, said holding means comprising a flexible wall portion having a slit formed therein,
    means cooperative with the slit of said holding means for injecting gas through the slit and substantially upwardly into said fluid to effect formation of bubbles passing substantially through said fluid and transporting some of said fluid above the surface of said fluid, and
    means cooperative with said holding means above said fluid surface for collecting said transported fluid only when said fluid coagulates.

2. The apparatus of claim 1 in which said holding means comprises an elongated vial.

3. The apparatus of claim 1 in which said injecting means comprises a gas supply and a nozzle cooperative with said gas supply for delivering gas into said fluid in said holding means.

4. The apparatus of claim 1 in which said collecting means comprises a gauze above said surface of said fluid.

5. An apparatus for accelerating and signalling the event of coagulation of blood and components thereof, said apparatus comprising:
    means for holding said blood, said holding means including a resiliently expandable slit formed therein,
    means cooperative with said holding means for injecting gas through the slit and into said blood, said injected gas effectuating the formation of bubbles transporting some of said blood above the surface of said blood,
    means cooperative with said holding means above said surface for collecting said transported blood from said bubbles only when said blood coagulates, and
    means cooperative with said holding means operative upon the drop in the level of said blood for generating a signal, said signal being indicative of said coagulation.

6. The apparatus of claim 5 in which said holding means comprises an elongated vial.

7. The apparatus of claim 5 in which said injecting means comprises a gas supply and a nozzle connected to said gas supply for delivering gas into said blood in said holding means.

8. The apparatus of claim 5 in which said collecting means comprises a gauze cooperative with said holding means above said surface of said blood for trapping said transported coagulated blood from said bubbles.

9. The apparatus of claim 5 in which said generating means comprises a light source for directing a beam of light through said blood and a photocell opposing said light source receptive of said beam when said surface of said blood drops below said beam in response to said collection for generating an electrical signal, said signal being indicative of said coagulation.

10. An apparatus for accelerating and signalling the event of coagulation of blood and components thereof, said apparatus comprising:
  means for holding said blood,
  means cooperative with said holding means for injecting gas into said blood, said injected gas effectuating the formation of bubbles transporting some of said blood above the surface of said blood,
  means cooperative with said holding means above said surface for collecting said transported blood from said bubbles only when said blood coagulates,
  means operative upon the drop in the level of said blood for generating a signal, said signal being indicative of said coagulation, and second means operative upon the presence of said bubbles above said surface for generating a second signal, said second signal being indicative that said gas is being injected into said blood.

11. The apparatus of claim 10 wherein said second means comprises a light source for directing a beam of light through the space above said surface of said blood and a photocell opposing said light source responsive to the presence of said light beam through said bubbles for generating said second signal.

12. An apparatus for signalling the event of coagulation of blood and components thereof, said apparatus comprising:
  a vial for holding said blood,
  a gas supply,
  a nozzle operative with said supply for injecting gas into said vial, said injected gas effectuating the formation of bubbles above the surface of said blood for transporting some of said blood,
  a gauze cooperative with the top of said vial and above the surface of said blood for collecting said transported blood from said bubbles only when said blood coagulates so that the level of said blood drops,
  a light source for directing a beam of light into said blood, said light source being positioned cooperatively with said vial to direct the beam of light below the surface level of blood prior to collection of blood from said bubbles and to direct the beam of light above the surface level of the blood upon collection of blood from said bubbles,
  a photocell opposing said light source receptive of said beam when said surface of said blood drops below said beam in response to said collection for generating an electrical signal, said signal being indicative of said coagulation, and
  a second light source for directing a beam of light through said vial at a point above said surface of said blood and a second photocell opposing said second light source responsive to the presence of said light beam through said bubbles for generating a second electrical signal, said second signal being indicative of the presence of said bubbles.

13. The apparatus of claim 12 further comprising means connected to said vial and receptive of said nozzle for providing a fluid communication between said vial and said nozzle.

14. An apparatus for signalling the event of coagulation of blood and components thereof, said apparatus comprising:
  a vial for holding said blood,
  a gas supply,
  a nozzle operative with said supply for injecting gas into said vial, said injected gas effectuating the formation of bubbles above the surface of said blood for transporting some of said blood,
  a gauze cooperative with the top of said vial and above the surface of said blood for collecting said transported blood from said bubbles only when said blood coagulates so that the level of said blood drops,
  a light source for directing a beam of light through said blood, and
  a photocell opposing said light source receptive of said beam when said surface of said blood drops below said beam in response to said collection for generating an electrical signal, said signal being indicative of said coagulation, and
  a second light source for directing a beam of light through said vial at a point above said surface of said blood and a second photocell opposing said second light source responsive to the presence of said light beam through said bubbles for generating a second electrical signal, said second signal being indicative of the presence of said bubbles.

15. The apparatus of claim 14 in which said providing means comprises a guide extending from said vial for guiding said nozzle and a cap disposed in said vial for detaching from said vial upon abutment by said nozzle.

16. An apparatus for signalling the event of coagulation of body fluid including blood after mixing said body fluid with a predetermined amount of additive, comprising:
  first means for holding a body fluid including blood,
  second means in selective communication with said first holding means for holding said additive,
  means for effecting selective communication between said first holding means and second holding means,
  means engaging said second holding means for releasing said communication means thereby injecting said additive into said fluid,
  means operative with said releasing means for delivering gas into the body fluid and additive mixture, said gas effectuating bubbles transporting some of said fluid above the surface of said fluid,
  means connected to said first holding means above said surface for collecing said transported fluid only when said body fluid coagulates, and
  means operative upon said collection for generating a signal, said signal being indicative of said coagulation.

17. The apparatus of claim 16 in which said first holding means comprises a vial.

18. The apparatus of claim 16 in which said injecting means comprises a nozzle cooperative with said delivery means for injecting gas into said second holding means.

19. The apparatus of claim 16 in which said collecting means comprises a gauze connected to said holding means above said surface of said fluid.

20. The apparatus of claim 16 in which said generating means comprises a light source for directing a beam of light through said fluid and a photocell opposing said light source receptive of said beam when said surface of said fluid drops below said beam in response to said collection for generating said signal.

21. The apparatus of claim 16 further comprising second means operative upon the presence of said bubbles above said surface for generating a second signal, said second signal being indicative that said gas is being injected into said fluid.

22. The apparatus of claim 21 wherein said second means comprises a light source for directing a beam of light through the space above said surface of said fluid and a photocell opposing said light surface responsive to the presence of said light beam through said bubbles for generating said second signal.

23. An apparatus for signalling the event of coagulation in blood and components thereof after mixing said blood with a predetermined amount of additive, said apparatus comprising:
 a vial for holding said blood,
 a chamber on the bottom of said vial for holding said additive,
 a releasable cap separating said chamber from said vial,
 a gas supply,
 a nozzle cooperative with said supply for releasing said cap and for collapsing said chamber so that said gas is delivered into the blood and additive mixture, said gas effectuating bubbles transporting some of said blood above the surface of said blood,
 a gauze connected to the top of said vial and above said surface for collecting said transported blood only when said blood coagulates, and
 means operative upon said collection for generating a signal, said signal being indicative of said coagulation.

24. The apparatus of claim 23 in which said generating means comprises a light source for directing a beam of light through said blood and a photocell opposing said light source receptive of said beam when said surface of said blood drops below said beam in response to said collection for generating an electrical signal.

25. The apparatus of claim 23 further comprising a second light source for directing a beam of light through said vial at a point above said surface of said blood and a second photocell opposing said second light source responsive to the presence of said light beam through said bubbles for generating a second electrical signal, said second signal being indicative of the presence of said gas.

26. The apparatus of claim 23 wherein said vial comprises inwardly and downwardly tapering sides.

27. The apparatus of claim 26 wherein said tapering sides are inclined in a range between 0.5° and 10° from vertical.

28. The apparatus of claim 23 in which said chamber comprises:
 a tubular protrusion downwardly extending from said releasable cap having a passageway formed therein, and
 a plug comprising:
 (a) an outer cylindrical wall, and
 (b) an inner hemispherical portion disposed within said wall, said hemispherical portion being integral with the bottom of said wall and further having the apex of said portion in substantially the same plane as the top of said wall, said plug being slideably disposed in said formed passageway with said apex of said hemisphere being directed toward said cap.

29. The apparatus of claim 28 wherein said outer cylindrical wall tapers outwardly from said bottom so that said plug firmly engages inner surface of said formed passageway of said protrusion.

30. The apparatus of claim 29 wherein the said cap has a downwardly protruding stem, said stem effecting said hemispherical portion of said plug to invert and protrude downwardly into said formed passageway.

31. The apparatus of claim 30 wherein said nozzle comprises a cylindrical portion and a needle portion disposed on the upper surface of said cylindrical portion for abutting the hemispherical portion of said plug below said stem, said cap releasing from said vial upon pressure by said nozzle on said stem, said pressure being transmitted through said hemispherical portion.

32. The apparatus of claim 31 wherein the diameter of said cylindrical portion is slightly less than the inner diameter of said formed passageway so that the upper surfaces of said cylindrical portion engage said bottom of said outer wall of said plug so that pressure by said nozzle on said plug causes said plug to move upwardly to abut the bottom of said vial thereby injecting said additive into said blood.

33. The apparatus of claim 32 wherein said upper surfaces of said cylindrical portion engage said bottom wall of said plug in an air-tight sealed relationship, said hemispherical portion having a slit opening on said apex being responsive to the delivery of gas from said needle for upwardly expanding and opening said slit so that said gas is delivered into said vial.

34. A method for detecting the coagulation of body fluids including blood comprising the steps of:
 injecting gas into the body fluid so that bubbles are formed above the surface of the fluid,
 generating a signal upon the presence of bubbles above the surface of the fluid indicative that gas is being injected,
 collecting the fluid from the bubbles above the surface of the fluid only when the body fluid coagulates, and
 generating a detection signal in response to a predetermined drop in the surface level of the fluid occurring due to said collection.

35. A method for neutralizing anticoagulated blood and components thereof and for accelerating and signalling the event of coagulation of said neutralized blood, said method comprising the steps of:
 injecting an additive into the anticoagulant blood, said additive being capable of neutralizing the anticoagulant in the blood,
 injecting gas into the blood, said gas being capable of accelerating coagulation and being further capable of generating bubbles on the surface of the blood,
 refluxing the liquid blood transported by the bubbles back into the sample in the vial before coagulation occurs,
 collecting the gel-like blood transported by the bubbles in an area above the surface of the sample when coagulation occurs, and
 generating a detection signal in response to the aforesaid collection, said signal being indicative of said coagulation.

36. An apparatus for selectively mixing a body fluid sample containing blood with an additive in response to an external force, said apparatus comprising:
 means for holding said fluid sample,
 a chamber situated on said means for holding said additive,
 a releasable cap between said holding means and said chamber;
 a tubular protrusion extending from said releasable cap having a passageway formed therein, and
 a plug comprising:
 (a) an outer cylindrical wall, and
 (b) an inner hemispherical portion disposed within said wall, said hemispherical portion being integral with the bottom of said wall and further having the apex of said portion in substantially the same plane as the top of said wall, said plug being slideably disposed in said formed passageway with said apex of said hemisphere being directed toward said cap.

37. The apparatus of claim 36 wherein said outer cylindrical wall tapers outwardly from said bottom so that said plug firmly engages the inner surface of said formed passageway of said protrusion.

38. The apparatus of claim 37 wherein the said cap has a downwardly protruding stem, said stem effecting said hemispherical portion of said plug to invert and protrude downwardly into said formed passageway.

39. The apparatus of claim 36 wherein said holding means comprises a vial having inwardly and downwardly tapering sides.

40. The apparatus of claim 39 wherein said tapering sides are inclined in a range between 0.5° and 10° from vertical.

41. Apparatus for selectively mixing reagents comprising:
a cell structure having an elongated bore extending generally longitudinally therethrough, the elongated bore having a side wall;
a cap member cooperative with the sidewall intermediate longitudinal ends of the bore to releasibly seal the the bore of said cell structure, said cap member and a portion of elongated bore on one side of said cap member defining a vial;
a plug member of elastic flexible material abutting to the sidewall and sealing the bore of said cell structure at a position spaced from said cap member on the side opposite the vial, the space between said plug member and said cap member defining a chamber; and
means in the chamber operatively interconnecting said plug and cap members for selectively releasing said cap member from a sealed relation with the sidewall of the bore when force is applied to said plug member.

42. Apparatus as recited in claim 44 wherein the sidewalls of the vial are tapered.

43. Apparatus as defined in claim 41 wherein said plug member comprises a sealing wall portion extending substantially transversely across the bore of said cell member.

44. Apparatus as recited in claim 43 wherein the sealing wall portion of said plug member comprises means for selectively passing gas through the sealing wall portion.

45. Apparatus as defined in claim 43 wherein said releasing means comprises a stem member attached to said cap member and extending toward the sealing wall portion of said plug member.

46. Apparatus as defined in claim 45 wherein the stem member deflects a portion of the sealing wall portion longitudinally away from said cap member.

47. Apparatus as defined in claim 46 wherein the sealing wall portion of said plug member comprises means for selectively passing gas through the sealing wall portion of said plug member.

48. Apparatus as defined in claim 47 wherein said means for selectively passing gas through the sealing wall portion comprises a slit formed in the sealing wall portion.

49. Apparatus as defined in claim 48 wherein said stem member contacts and deflects the sealing wall portion of said plug member at the slit to seal the slit when the sealing wall portion is deflected.

50. An apparatus for accelerating and signalling the event of coagulation of blood and components thereof, said apparatus comprising:
means for holding blood,
means cooperative with said holding means for injecting gas into the blood, said injected gas effectuating the formation of bubbles to transport some of the blood above the surface of the blood,
means cooperative with said holding means above the surface of the blood for collecting transported blood from the bubbles only when the blood coagulates,
means cooperative with said holding means and said collecting means for directing a beam of light to detect the condition of collection of substantially all of the blood of the bubbles at said collective means,
means, operative upon blood collection by said collecting means annd operative in conjunction with said light beam directing means, for generating a signal, said signal being indicative of coagulation at said collecting means, and
second means operative upon the presence of the bubbles above the surface of the blood for generating a second signal, said second signal being indicative that said gas is being injected into said blood.

51. The apparatus of claim 50 wherein said second means comprises a light source for directing a second beam of light through the space above the surface of the blood and a photocell opposing the light source responsive to the presence of the second light beam through the bubbles for generating said second signal.

* * * * *